United States Patent
Lura et al.

(10) Patent No.: US 10,874,788 B2
(45) Date of Patent: Dec. 29, 2020

(54) INFUSATE CADDY FOR A DIALYSIS SYSTEM

(71) Applicant: Medtronic, Inc., Minneapolis, MN (US)

(72) Inventors: David B. Lura, Maple Grove, MN (US); Christopher M. Hobot, Tonka Bay, MN (US); Martin T. Gerber, Maple Grove, MN (US); Thomas E. Meyer, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 104 days.

(21) Appl. No.: 15/219,238

(22) Filed: Jul. 25, 2016

(65) Prior Publication Data

US 2017/0021079 A1 Jan. 26, 2017

Related U.S. Application Data

(60) Provisional application No. 62/196,891, filed on Jul. 24, 2015.

(51) Int. Cl.
*A61M 1/16* (2006.01)
*A61M 1/26* (2006.01)

(52) U.S. Cl.
CPC ........ *A61M 1/1668* (2014.02); *A61M 1/1656* (2013.01); *A61M 1/267* (2014.02); *A61M 2205/6036* (2013.01); *A61M 2209/08* (2013.01)

(58) Field of Classification Search
None
See application file for complete search history.

(56) References Cited

U.S. PATENT DOCUMENTS

| 1,683,723 A | 9/1928 | William |
| 4,747,822 A | 5/1988 | Peabody |
| 4,950,230 A * | 8/1990 | Kendell ................. A61M 1/28 137/625.41 |
| 5,032,265 A | 7/1991 | Jha |
| 5,643,201 A | 7/1997 | Peabody |
| 5,744,031 A | 4/1998 | Bene |

(Continued)

FOREIGN PATENT DOCUMENTS

| CN | 202105667 | 1/2012 |
| EP | 2735322 | 5/2014 |

(Continued)

OTHER PUBLICATIONS

International Search Report, Application PCT/US2016/043948, dated Feb. 2, 2017.

(Continued)

*Primary Examiner* — Jonathan M Peo
(74) *Attorney, Agent, or Firm* — Hahn & Associates PLLC; Roger Hahn

(57) ABSTRACT

The invention relates to an infusate caddy for carrying, organizing, and operating infusate containers containing solutes for preparing dialysate and related fluids for use in dialysis. The infusate containers can be seated in the infusate caddy, and the infusate containers removed from the infusate caddy for restocking, cleaning, or resupply, as needed. The infusate caddy can be positioned or seated in a receiving compartment of a dialysis machine, and can also be removed, as needed, from the dialysis machine.

23 Claims, 9 Drawing Sheets

(56) References Cited

U.S. PATENT DOCUMENTS

| | | | |
|---|---|---|---|
| 6,355,161 B1 | 3/2002 | Shah | |
| 6,645,191 B1 * | 11/2003 | Knerr | A61J 1/2093 604/410 |
| 9,511,182 B2 * | 12/2016 | Balschat | A61M 1/1656 |
| 2002/0091371 A1 | 7/2002 | Ritter | |
| 2010/0051552 A1 | 3/2010 | Rohde | |
| 2010/0078092 A1 * | 4/2010 | Weilhoefer | A61M 1/1656 141/9 |
| 2010/0312172 A1 | 12/2010 | Hoffman | |
| 2011/0017665 A1 | 1/2011 | Updyke | |
| 2011/0249916 A1 | 10/2011 | Herrenbauer | |
| 2012/0199205 A1 * | 8/2012 | Eyrard | A61M 1/1656 137/1 |
| 2013/0001165 A1 * | 1/2013 | Pohlmeier | A61M 1/1656 210/646 |
| 2013/0015302 A1 * | 1/2013 | Orter | A61M 1/1656 248/129 |
| 2013/0062265 A1 | 3/2013 | Balschat | |
| 2014/0018727 A1 | 1/2014 | Burbank | |
| 2014/0217029 A1 | 8/2014 | Meyer | |
| 2017/0021079 A1 | 1/2017 | Lura | |

FOREIGN PATENT DOCUMENTS

| | | | | |
|---|---|---|---|---|
| JP | 2006325668 A | 12/2006 | | |
| WO | 9937342 A1 | 7/1999 | | |
| WO | 0057935 | 10/2000 | | |
| WO | WO-0057935 A1 * | 10/2000 | | A61L 2/0023 |
| WO | WO2009064984 | 5/2009 | | |
| WO | 2011113572 A1 | 9/2011 | | |
| WO | 2012138604 A2 | 10/2012 | | |
| WO | 2014121158 A1 | 8/2014 | | |
| WO | 2015071247 A1 | 5/2015 | | |
| WO | WO2017/019640 A1 | 2/2017 | | |

OTHER PUBLICATIONS

Written Opinion, Application PCT/2016/043948, dated Feb. 2, 2017.
International Search Report, Application PCT/US2016/043935, dated Feb. 2, 2017.
Written Opinion, Application PCT/US2016/043935, dated Feb. 2, 2017.
International Preliminary Report on Patentability, Appliaction PCT/US2016/043950, dated Jul. 31, 2017.
International Preliminary Report on Patentability, Appliaction PCT/US2016/043935, dated Jul. 17, 2017.
Internation Preliminary Report on Patentability, Application PCT/US2016/043948, dated Jul. 17, 2017.
Written Opinion, Application PCT/US2016/043935, dated Jun. 21, 2017.
[NPL636] Written Opinion, Application PCT/2016/043948, dated Feb. 2, 2017.
[NPL635] International Search Report, Application PCT/US2016/043948, dated Feb. 2, 2017.
[NPL638] Written Opinion, Application PCT/US2016/043935, dated Feb. 2, 2017.
[NPL637] International Search Report, Application PCT/US2016/043935, dated Feb. 2, 2017.
European Office Action for App. No. 16757383.1, dated Mar. 13, 2020.
European Office Action for App. No. 17724468.8, dated May 14, 2020.
Chinese Office Action for App. No. 201680041324.7, dated Jun. 1, 2020.
Chinese Office Action for App. No. 201680041413.1, dated May 28, 2020.
European Search Report for App. No. 16760215.0, dated May 7, 2020.
European Search Report for App. No. 17724689.9, dated May 14, 2020.
Chinese Office Action for App. No. 201680041414.6, dated Jun. 9, 2020.
Chinese Office Action for App. No. 201680041414.6, dated Oct. 20, 2020.

* cited by examiner

INFUSATE CADDY FOR A DIALYSIS SYSTEM

FIELD OF THE INVENTION

The invention relates to an infusate caddy for carrying, organizing, and operating infusate containers containing solutes for preparing dialysate and related fluids for use in dialysis. The infusate containers can be seated in the infusate caddy, and the infusate containers removed from the infusate caddy for restocking, cleaning, or resupply, as needed. The infusate caddy can be positioned or seated in a receiving compartment of a dialysis machine, and can also be removed, as needed, from the dialysis machine.

BACKGROUND

Dialysis systems require specific and precise amounts of specific solutions to be used during each dialysis session, such as sodium chloride, sodium bicarbonate, and cation infusates. Further, many cations, such as potassium, calcium and magnesium, can cross the dialyzer and be removed from a patient during dialysis. The cations must be added back into the dialysate to maintain the concentration of these cations at a desired level. Sodium bicarbonate can be used during dialysis as a buffer to control the pH of the dialysate and to treat acidosis by delivering bicarbonate across the dialysis membrane to the patient receiving a treatment. The amounts of sodium chloride, sodium bicarbonate and other cations added to dialysate should be closely monitored and controlled. Further, the amounts of each of these solutions necessary can vary considerably.

A system and method for ensuring proper solutes are added in proper amounts to the dialysate are required. To facilitate use of dialysis by personnel, systems and methods are needed that can ensure that any of the solutes, solution, components, materials to be used during dialysis and added back to the dialysis system can be connected to the correct pumps, valves and connectors of the dialysis machine and related flow paths. Further, systems and methods are needed to ensure that all necessary components to be used during dialysis are connected to the dialysis system at the correct locations for a dialysate flow path. There is a further need for a method and system that can ensure proper disinfection of a dialysis system after a dialysis session is complete. A system can allow users of varying skill levels to easily configure the dialysis system for disinfection, and ensure that the dialysis system can be used outside of a clinical setting, such as in a patient's home, is needed.

SUMMARY OF THE INVENTION

The first aspect of the invention relates to an infusate caddy for use with a dialysis machine. In any embodiment of the first aspect of the invention, the infusate caddy can have a bottom and at least one side extending upwardly from the bottom to form a shape complementary to a receiving compartment on a dialysis machine; and at least one receiving compartment disposed on the infusate caddy complementary to an infusate container wherein the receiving compartment has at least one fitting feature complementary to a corresponding fitting feature of the infusate container.

In any embodiment, the shape complementary to the receiving compartment on the dialysis machine can be any one of a cube, disc, ovoid, or triangular prism.

In any embodiment, the receiving compartment disposed on the infusate caddy can be aligned to a fluid connector disposed on the dialysis machine.

In any embodiment, the fluid connector can form a fluid connection between the infusate container and a flow path inside the dialysis machine.

In any embodiment, the infusate caddy can have a collapsible handle integral to the infusate caddy.

In any embodiment, the fitting feature complementary to the corresponding fitting feature of the infusate container can be selected from the group of a protrusion, an indentation, a groove, and a ridge.

In any embodiment, any one of the protrusion, indentation, groove, or ridge can be complementary to a corresponding indentation, a corresponding protrusion, a corresponding ridge, or a corresponding groove on the infusate container.

In any embodiment, the fitting feature can be selected from any one of a specified geometry, size, or shape.

In any embodiment, any one of the specified geometry, size, or shape can be complementary to a corresponding geometry, a corresponding size, or a corresponding shape of the infusate container.

In any embodiment, the infusate caddy can have an infusate caddy locking mechanism.

In any embodiment, the fitting feature can be positioned on an interior surface of the receiving compartment.

In any embodiment, the fitting feature can be a locking mechanism keyed to the infusate container.

In any embodiment, the infusate caddy can include a visual indicator indicative of proper seating of the infusate container in the infusate caddy.

In any embodiment, the infusate container can be selected from the group of a sodium bicarbonate container, a sodium chloride container, and a cation container.

In any embodiment, the infusate caddy can include a receiving compartment for a citric acid container.

In any embodiment, the citric acid container can have at least one fluid connection to allow recirculation between two or more fluid connectors.

In any embodiment, the fitting feature can be selected from any one of a specified geometry, size, or shape of a first infusate container and a complementary geometry, size, or shape of a second infusate container.

In any embodiment, the fitting feature can be a curved wedge protrusion disposed on an interior side of the infusate caddy.

The features disclosed as being part of the first aspect of the invention can be in the first aspect of the invention, either alone or in combination.

The second aspect of the invention is drawn to a dialysis system. In any embodiment, the dialysis system can include an infusate caddy having one or more infusate containers containing one or more solute; a dialysis machine having (i) a dialysate flow path, (ii) a receiving compartment adapted to receive the infusate caddy, and (iii) one or more fluid connectors fluidly connectable to the one or more infusate containers.

In any embodiment, the dialysis system can include one or more pumps and one or more valves positioned on the one or more dialysis machine connectors; the one or more pumps and one or more valves controlling fluid flow from the one or more infusate containers into the one or more fluid connectors.

In any embodiment, the dialysis system can include a control system, wherein the control system controls the one or more pumps and the one or more valves to selectively flow fluid from the one or more infusate containers into the dialysate flow path.

In any embodiment, the fluid connectors can include a length of hose, wherein each length of hose is alternatively connectable to each of the one or more infusate containers.

In any embodiment, the dialysis system can include a paddle assembly having one or more paddles; wherein each of the one or more paddles are alternatively connectable to each of the one or more infusate containers depending on an orientation of the infusate caddy in the dialysis machine.

In any embodiment, the paddles can be lockable paddles configured to lock each of the infusate containers in place.

In any embodiment, the paddles can include the fluid connectors.

In any embodiment, the system can include a locking mechanism configured to keep the infusate caddy from moving after insertion into the receiving compartment when the locking mechanism is in a locked state.

In any embodiment, the locking mechanism can be positionable in an open state wherein the open state allows removal of the infusate caddy.

In any embodiment, at least one pump can be capable of moving fluid bi-directionally through the dialysis machine connectors.

In any embodiment, the infusate caddy can be insertable into the receiving compartment in at least a first orientation and a second orientation.

In any embodiment, the infusate caddy can be configured such that one or more infusate containers are connectable to the dialysis machine in the first orientation, but not in the second orientation.

In any embodiment, in the second orientation, the infusate caddy can be rotated between 1° and 359° from the first orientation.

In any embodiment, in the second orientation, the infusate caddy can be rotated about 180° from in the first orientation.

In any embodiment, at least one fluid connector can be sealed when the infusate caddy is inserted into the receiving compartment in the second orientation.

In any embodiment, at least two fluid connectors can be connected to allow recirculation flow between the connectors when the infusate caddy is inserted into the receiving compartment in the second configuration.

In any embodiment, the infusate caddy can contain a disinfection container.

In any embodiment, the disinfection container can be connectable to one or more of the fluid connectors when the infusate caddy is in the second orientation.

In any embodiment, the disinfection container can contain citric acid.

In any embodiment, the dialysis system can include a second infusate caddy, wherein the second infusate caddy has one or more containers fluidly connectable to the one or more fluid connectors; and wherein the receiving compartment is adapted to receive the second infusate caddy.

In any embodiment, the second infusate caddy can contain a disinfection container.

In any embodiment, the disinfection container can contain citric acid.

In any embodiment, the infusate caddy can have a sensor; wherein the sensor determines whether the infusate caddy is in the first orientation or the second orientation.

In any embodiment, the system can include a tracking component on the infusate caddy.

In any embodiment, the tracking component can track whether the infusate caddy is matched to a particular dialysis machine and/or a particular patient.

In any embodiment, the tracking component can determine whether the infusate containers in the infusate caddy match a dialysis prescription of a patient.

The features disclosed as being part of the second aspect of the invention can be in the second aspect of the invention, either alone or in combination.

DETAILED DESCRIPTION OF THE INVENTION

Figure 1:
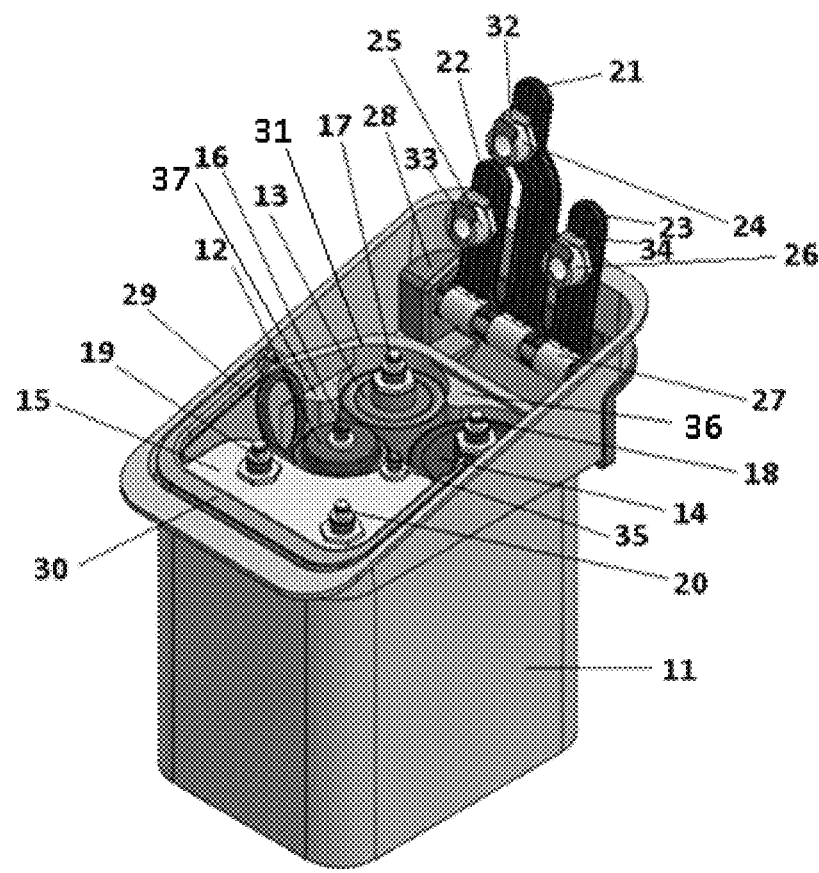
FIG. 1 shows an infusate caddy containing infusate containers.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The term "adapted to receive" refers to a component capable of holding one or more chemicals, chemical solutions, containers or any other component.

The terms "aligned" or "in alignment" refers to two components or features that are positioned so that a connection can be formed between the components.

The term "alternatively connectable" refers to a connector that can form a connection with a first component or container but not a second component or container.

The term "bicarbonate container" or "sodium bicarbonate container" refers to a container that can be a stand-alone container or alternatively can be integrally formed with an apparatus for hemodialysis, hemodiafiltration, or hemofiltration. The bicarbonate container can store a source of buffering material, such as sodium bicarbonate, and can be configured to interface with at least one other functional module found in systems for hemodialysis, hemodiafiltration, or hemofiltration. The bicarbonate container can contain at least one fluid pathway and include components such as conduits, valves, filters or fluid connection ports. The bicarbonate container may be single use, or may be refilled and used multiple times, for example, by refilling the bicarbonate container to replace the bicarbonate material which can be a liquid or solid form.

The terms "bi-directional" or "moving fluid bi-directionally" refers to the ability to move fluid in more than one direction through a fluid flow path. A pump that is capable of moving fluid bi-directionally can move fluid in one direction through a fluid flow path and then switch to move fluid in the opposite direction through the fluid flow path. The bi-directional fluid flow can also be accomplished by more than one pump capable of moving fluid in opposite directions.

The term "bottom" refers to a base of a component when the component is positioned for normal use.

A "curved wedge protrusion" is a fitting feature extending inwardly towards the center of the compartment. The curved wedge protrusion in one, non-limiting embodiment can be disposed on an interior side of a receiving compartment.

The term "fluid connector" refers to a mechanism or feature that can securely connect one component to a second component such that fluid can flow across the connector. In one non-limiting example, a fluid connector can make a secure connection between a dialysate flow path in a dialysis machine and an infusate container seated in an infusate caddy.

The term "cantilevered paddle" refers to a paddle extending outwardly from a paddle support and moveable or rotatable about the support such as a hinge.

The term "cation infusate container" refers to a source from which cations can be obtained. Examples of cations include, but are not limited to, calcium, magnesium and potassium. The source can be a solution containing cations or dry compositions that are hydrated by the system. The cation infusate container is not limited to cations and may optionally include other substances to be infused into a dialysate or replacement fluid; non-limiting examples can include glucose, dextrose, acetic acid and citric acid.

A "citric acid solution" is a solution containing citric acid, $C_6H_8O_7$, dissolved in water.

A "collapsible handle" is a component on an infusate caddy that can be used to hold the infusate caddy while moving the infusate caddy. The collapsible handle can be moved, or fold, to a side of the infusate caddy.

The term "complementary" as used to describe fitting features, refers to one or more fitting features on a first component that are designed to pair or mate with one or more fitting features on a second component. For example, a first component may have a receiving compartment of particular dimensions, and the second component may be the same dimensions, such that the second component can mate within the receiving compartment.

The term "comprising" includes, but is not limited to, whatever follows the word "comprising." Use of the term indicates the listed elements are required or mandatory but that other elements are optional and may be present.

The term "configured" means any particular form, alignment, shape, design, marking, or arrangement of a component suitable for performing a described function.

The term "configured to lock" means a form, alignment, shape, design, or arrangement of a component designed to attach to a second component, keeping the second component in place.

"Connectable" refers to two components that can be attached. In any embodiment, connectable components can be fluidly connectable if a secure, water-tight connection can be formed.

A "connector" and "for connection" can be used to describe the concept of forming a fluid connection between two components wherein fluid or gas can flow from one component, through a connector or a component for connection, to another component. The connector provides for a fluid connection in its broadest sense and can include any type of tubing, fluid or gas passageway, or conduit between any one or more components of the invention.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

A "control system" comprises combinations of components that act together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

The term "controlling fluid flow" or to "control fluid flow" refers to the ability to cause a fluid to move through a flow path in a specific direction, rate, or route.

The term "corresponding" as used to refer to fitting features refers to a fitting feature on one component and a complementary fitting feature on a second component.

The term "cube" refers to a three-dimensional shape having 6 faces at meeting at right angles, the six faces having substantially the same dimensions.

The term "detachable" or "detachably connect" relates to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

A "dialysate flow path" or "dialysate flow loop" is the route in which a fluid can travel during dialysis.

A "dialysis machine" is a system comprising a dialyzer, pumps, valves and fluid lines that is used to carry out a dialysis session.

A "fluid connector" is a connector for securely making a fluid connection between two or more components. In one non-limiting example, a dialysis flow path in a dialysis machine can be in fluid communication to an external component, such as an infusate container via the fluid connector.

The term "disc" refers to a substantially round shape. The sides of the disc can extend downwardly to form a cylinder of any volume or length.

A "disinfection container" is a source from which a disinfection solution, such as citric acid, can be obtained. The source can be a solution containing disinfecting chemicals or dry compositions that are hydrated by the system.

The term "disposed" refers to a first component's placement on a second component.

The terms "extending upwardly" or "upwardly extending" make reference to a feature, such as a wall or a side of geometric shape, that can be used to form a volume from a geometric based of any type. For example, a rectangular base having four sides can extend upwardly to form a cubic volume.

A "fitting feature" is any protrusion, indentation, groove, ridge, having any shape, size, or geometry that serves to ensure that only a corresponding fitting feature complementary to the fitting feature is capable of forming a connection or fit to the corresponding fitting feature. The fitting feature also includes non-mechanical means for ensuring complementary connection such as magnets placed at particular locations, or visual or aural indicators such as color, lettering, or sound. The fitting feature can be affixed, integral, or labeled on a component or surface to ensure that a corresponding feature on a desired component or surface can mate or connect to the component or surface having the fitting feature.

A "fluid" is a liquid substance optionally having a combination of gas and liquid phases in the fluid. Notably, a liquid can therefore also have a mixture of gas and liquid phases of matter.

The term "fluid connection," "fluidly connectable" or "fluidly connected" refers to the ability to pass fluid, gas, or mixtures thereof from one point to another point. The two points can be within or between any one or more of compartments, modules, systems, and components, all of any type.

The terms "fluid flow path," "pathway," and "flow path" refer to the route through which a fluid or gas, or both, such as dialysate or blood, travels. "Geometry" refers to the size or shape of a component.

A "groove" is an indentation in a component extending in two directions.

An "indentation" refers to a portion of a component wherein the portion extends inwardly from the base, exterior, or interior of the compartment.

The term "indicative of proper seating" refers to an indication that a container or component is situated within or on a second component in an intended position and space, allowing proper use of the container or component.

The term "infusate caddy" or "caddy" refers to a container detachably removable from a dialysis system, the caddy configured to hold one or more other containers. The caddy can be shaped to fit inside a receiving compartment, and can be used to carry, organize, or store containers or canisters.

An "infusate container" is a container adapted to contain one or more fluids. The infusate container can at times hold dry chemicals that are later able to be reconstituted with a fluid to form a further useable fluid within the system. The infusate container can also contain liquid solutions.

The terms "insertable" and "insertion" refer to the ability to place one component at least partly inside a receiving compartment or other component.

The term "integral" or "integrally formed" refers to a portion of a component that is either permanently attached to, or constructed from the component.

The term "interior surface" refers to an interior boundary of a component.

The term "keyed to an infusate container" refers to a locking mechanism sized or shaped to only engage and lock an infusate container having a complementary size or shape, or a connector of a complementary size and shape.

A "length of hose" refers to any flexible or semi-rigid fluid connector.

To "lock" means to connect two components such that the components will resist inadvertent detachment.

A "locked state" refers to a configuration of attached components wherein the components cannot easily be detached from one another.

A "locking mechanism" is any mechanism by which one component can be connected to a second component and resist inadvertent disconnection.

The term "matched to a particular" dialysis machine or patient refers to an infusate caddy specifically intended to be used by a particular patient, or with a particular dialysis machine.

The phrase "match a dialysis prescription" refers to a solution or concentrate having a concentration or solute profile prescribed by a health care professional for use by a patient in dialysis. The dialysis prescription can include the length and frequency of dialysis therapy.

"Moving fluid bi-directionally" or to "move fluid bi-directionally" refers to the ability of a system to cause fluid to move through a fluid line in either direction. The movement of fluid bi-directionally can be accomplished by a single pump capable of moving fluid in two directions, or by multiple pumps capable of moving fluid in opposite directions.

An "open state" refers to a configuration of attached components wherein the components can be detached from one another.

The term "orientation" refers to a direction a component, such as an infusate caddy is facing, when inserted into another component.

The term "ovoid" refers to a two-dimensional shape having rounded ends and a slightly elongated shape.

The term "paddles" refers to components that can be rotatable, and in a preferred embodiment the paddles rotationally extend axially from a central axis. Multiple paddles can be used together as a "paddle assembly."

The term "positionable" refers to the ability of a component to occupy a particular space or adopt a particular configuration.

A "protrusion" refers to a portion of a component wherein the portion extends outwardly from a base, exterior, or interior of a component.

The term "pump" refers to any device that causes the movement of fluids or gases by applying suction or pressure.

A "receiving compartment" is a portion of a container, caddy, device, or system adapted for receiving a component or container.

The terms "recirculation" or to "recirculate" refers to the movement of fluid in a flow loop from a first location, through the flow loop, back to the first location.

A "ridge" is a protrusion extending in two directions.

The term "sealed" refers to a state of a component that will prevent entry or exit of a fluid.

The term "seating" refers to the positioning of a component on or in a second component.

The term "selectively flow fluid" refers to controlling the movement of fluid in a specific route for a particular time, frequency, or rate.

The term "sensor" refers to a component capable of measuring a property or condition of a system.

"Shape" refers to the three dimensional form of a component.

The term "side" refers to a portion of a component upwardly extending from a base of the component.

"Size" refers to the area, surface area, or volume of a container or component.

The terms "sodium bicarbonate reservoir" and "sodium bicarbonate container" refer to an object that can be a stand-alone enclosure or alternatively can be integrally formed with an apparatus for hemodialysis, hemodiafiltration, or hemofiltration. The object can store a source of sodium bicarbonate in solid and/or solution form, and can be configured to interface with at least one other functional module found in systems for hemodialysis, hemodiafiltration, or hemofiltration. The sodium bicarbonate reservoir or container can contain at least one fluid pathway and include components such as conduits, valves, filters or fluid connection ports.

The terms "sodium chloride reservoir" and "sodium chloride container" refer to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. The sodium chloride reservoir or container can contain at least one fluid pathway and include components such as conduits, valves, filters or fluid connection ports.

A "solute" is a substance dissolved in, or intended to be dissolved in, a solvent.

The term "tracking component" can refer to a component affixed to a second component, wherein the tracking component can track the usage of the second component.

The term "triangular prism" refers to a three-dimensional shape having a planar base and inwardly tapering sides meeting at a central point above the base.

A "valve" is a device capable of directing the flow of fluid or gas by opening, closing or obstructing one or more pathways to allow the fluid or gas to travel in a path. One or more valves configured to accomplish a desired flow can be configured into a "valve assembly."

A "visual indicator" is any visible indication of a particular position for a component. The visual indicator can be a color coding system, a label, or any other system that informs a user of an intended position for a component.

Infusate Caddy

In FIG. 1, the infusate caddy 30 can be placed in a receiving compartment 11 positioned on a top console portion of a dialysis machine. The infusate caddy 30 can be shaped to contain one or more receiving compartments in which infusate containers that contain the ion sources, infusates, electrolytes, other solutes, or combinations thereof, needed for dialysis, can be seated or positioned. The infusate caddy 30 can have a fitting feature inside the receiving compartment such as a protrusion, indentation, groove, or ridge positioned wherein the fitting feature has any shape, size, or geometry that is complementary to a corresponding fitting feature on the infusate containers. For example, the fitting feature can be positioned on an interior surface of the receiving compartment of the caddy 30, wherein the receiving compartment is designed to receive an infusate container designed to occupy a unique position inside the caddy 30. In one-non-limiting example, a curved wedge protrusion 37 and a curved wedge protrusion 36 are positioned on the walls of the receiving compartment of the infusate caddy 30. The respective radii of the cation infusate container 12 and the sodium bicarbonate container 13 can be sized to be positioned appurtenant to curved wedge protrusion 37. Similarly, the respective radii of sodium bicarbonate container 13 and sodium chloride container 14 can be sized to be positioned appurtenant to curved wedge protrusion 36. Each of the infusate containers can have unique shape and/or size to ensure that the infusate container is not inadvertently placed in the wrong receiving compartment of the infusate caddy 30. Optionally, a corresponding fitting feature can be positioned on a surface of the infusate container to ensure that the infusate container correctly mates or connects to the infusate caddy 30 at a unique position when placed inside the receiving compartment of the caddy 30.

The fitting feature is not limited to protrusions, indentations, grooves, or ridges, and can include any size and/or shape of the receiving compartment or of the container. For example, a depth, incline, or diameter of the receiving compartment of the caddy 30, can serve as a fitting feature and serve as a complementary surface. In such a case, the corresponding fitting feature can be an exterior surface shape, diameter, length, or curvature of an infusate container designed to fit inside the infusate caddy 30. Similarly, an exterior surface of the infusate caddy 30 can have fitting features to be complementary to the receiving compartment 11 on the top portion of the dialysis machine 11. Similar to the receiving compartments of the infusate caddy 30, the receiving compartment 11 of the dialysis machine, can also have a specified fitting feature positioned on an interior surface as a curved wedge protrusion.

The ion sources and infusates sources can include cation infusate container 12, sodium bicarbonate container 13 and sodium chloride container 14. One skilled in the art will understand that the caddy 30 or any one of the containers can have any number of different combinations, shapes, and sizes in addition to those shown in FIG. 1. The one or more fitting feature can include a visual indicator of the position of each of the containers, such as by labeling or color coding to indicate the correct position of each of the containers. For example, a label or color code can be affixed to indicate the correct position of each of the containers. The correct position of the sodium bicarbonate container receiving compartment can be colored blue, and the corresponding sodium bicarbonate container can also be colored blue. The correct position for the cation infusate container can be red, and the cation infusate container can also be red. The user can simply match the blue container to the blue position in the caddy, and the red container to the red position in the caddy. One of skill in the art will understand that any color or visual coding system including letters and symbols can be used to indicate the correct position for each container. The fitting feature can also be non-mechanical means for ensuring complementary connection such as magnets placed at particular locations in the infusate caddy 30. The caddy 30 can include fitting features that ensure specific containers can only occupy specific positions within the caddy 30. Further, the caddy 30 can contain more or less than four containers. Any combination of fitting features can be used together. For example, an infusate container can have a color code, a magnet of proper polarity, and a groove for proper mating to a corresponding receiving compartment in the infusate caddy 30. The caddy 30 can have a handle for easy removal of the container.

Multiple infusate sources can be used in the caddy with other ions necessary for a dialysis session. The solute containers can contain an enzyme, such as urease, for addition to a sorbent cartridge, and other solutes for removal or control over concentrations of solutes in the dialysate, such as barium carbonate for control over sulfate in the dialysate. Any number of containers can be connected to any number of connectors. Each infusate can be in a separate container, such as a magnesium infusate container, a potassium infusate container and a calcium infusate container. Additionally, any of the containers shown in the figures can be avoided in the caddy 30.

Each of the containers can include a fluid connector for fluid connection to the dialysis system, such as connector 16 on cation infusate container 12, connector 17 on sodium bicarbonate container 13 or connector 18 on sodium chloride container 14. The fluid connectors may have affixed thereon, or may itself, be a fitting feature, as described herein, such that the fluid connectors can connect to a particular infusate container having a corresponding fitting for placement of the infusate container into the caddy 30 at the appropriate location. One or more valves (not shown in FIG. 1) can be included on the connectors to control the movement of fluid from the containers, through the connectors and into the dialysis system. One or more valves may also be included on connectors in the dialysis system fluidly connected to the connectors 16, 17, and 18 in order to control the movement of fluid from the containers through the connectors and into the dialysis system. Check valves (not shown) or a poppet type valve can be included on connectors 16, 17, and 18 to limit direction of flow to be unidirectional, or to prevent spillage when the connectors are disengaged. The valves may be 2-way, 3-way, 4-way or any other type of valve. The valves may be configured such that fluid can move through the connectors bi-directionally, that is, fluid may move from the containers into the dialysis system, or fluid may move from the dialysis system and into the containers. The connectors can be configured so both gas and liquid may move through the valves and into or out of the containers.

Any of the connectors can be coaxial connectors. Coaxial connectors allow simultaneous fluid ingress and fluid egress from the container through a single connector. Using coaxial connectors allows solid solute sources to be used in each of the containers because fluid can be directed into the containers to dissolve the solid solute, creating a solute solution, and then the solute solution can be added into the dialysis circuit. Using coaxial connectors also allows pressure equalization in the containers as fluid is added or removed, because gas can also be added or removed from the container at the same time.

The caddy 30 can also include a disinfection container, such as citric acid container 15. After dialysis is complete, the user can disconnect or remove sodium chloride container 14, sodium bicarbonate container 13, and cation infusate container 12, and connect the dialysis machine to citric acid container 15 through connectors 19 and 20. Citric acid can be moved from the citric acid container 15 into the fluid lines of the dialysis system to disinfect the system and prepare the system for the next use. The caddy 30 can be moved into a disinfection configuration as described in order to place citric acid container 15 in position for connection to the dialysis machine. Any of the containers can contain a solid material that can be dissolved to create the appropriate solution, such as solid sodium chloride in sodium chloride container 14. Water may be added to the sodium chloride container 14 through connector 18 during the priming and set up of the dialysis system. Because the sodium container 14 contains an amount of sodium chloride solids, when an amount of water is added to sodium chloride container 14, the resulting sodium chloride solution produced in sodium chloride container 14 will be approximately saturated and thus of a known concentration. The sodium chloride solution can then be used during dialysis. Similarly, the sodium bicarbonate container 13 can contain sodium bicarbonate solids and the cation infusate container 12 can contain a solid source of cations of a known mass, each of which can be dissolved with a known amount to of water to create a fluid for dialysis. The cations can be present in cation infusate container 12 as a pre-mixed liquid which can be used in dialysis without additional water being added to cation infusate container 12 by the system.

The caddy 30 can include caddy connectors for connection to the connectors on each of the containers in the caddy. As shown in FIG. 1, the caddy connectors can be included on paddles 21, 22, and 23. The caddy connectors can connect to dialysis machine connectors for addition of the solute solutions into the dialysis system. The caddy 30 may include components for securing each of the containers in the proper location within the caddy 30 for proper connection to the dialysis machine. Furthermore, an exterior surface of the caddy connectors can have a fitting feature to ensure proper mating to corresponding infusate container. For example, a first caddy connector can have a hexagonal-shape while a second caddy connector can have a circular-shape. The corresponding infusate containers can have surfaces matched to receive the hexagonal- or circular shaped caddy connectors. One skilled in the art will understand that additional solute containers can be included in the caddy, and that additional paddles and connectors can be included as necessary.

The caddy connectors need not be included on paddles, and can be a length of hose, wherein the hose is fluidly connected to a dialysate flow path. The hose can be made of any material known in the art for use in dialysis systems, including silicone, reinforced silicone, or PVC. One skilled in the art will understand that other biocompatible materials can be used for the hose, and the hose is not limited to these materials. The hoses can be either flexible or semi-rigid, which would allow the hoses to move for connection to the containers in the caddy. The hoses can be sized and positioned such that each hose will only be able to connect with a single container within the caddy. For example, each hose may be positioned on a specific location with respect to the caddy, and each hose can be short enough so that the hose cannot reach any container not aligned with the specific location.

In FIG. 1, the locking mechanism can be a portion of paddle assembly 28. Each of the paddles 21, 22 and 23 in paddle assembly 28 can include a locking connector, such as caddy connector 24 on paddle 21, caddy connector 25 on paddle 22 and caddy connector 26 on paddle 23. After the infusate containers are properly placed inside the caddy 30, the paddles of the assembly 28 can be lowered and connected to corresponding container connectors 16, 17, and 18 on the containers within the caddy 30. The configuration of assembly 28 and caddy 30 can ensure that the correct connectors will be aligned to the correct container to prevent connection errors by the user. The paddles of the paddle assembly 28 can be lowered by pivoting the paddles on hinge 27. The caddy connectors 24, 25, and 26 can fit over the container connectors 16, 17, and 18, respectively. The caddy connectors 24, 25, and 26 can be tightened to lock the containers in place by twisting the caddy connectors 24, 25, and 26. Once tightened, the caddy connectors 24, 25, and 26 can lock the containers in place and resist inadvertent disconnection. The paddle assembly 28 can include a locking mechanism (not shown), so that after the paddles are lowered and locked into place, the paddles will resist inadvertent movement in a vertical and/or lateral direction. Further, the caddy connectors can include a locking mechanism 32 as shown on caddy connector 24, locking mechanism 33 as shown on caddy connector 25 and locking mechanism 34 as shown on caddy connector 26, each of which can lock the paddles on to the container connectors 16, 17, and 18.

The paddle assembly 28 may be constructed as part of a dialysis machine and positioned in a top section of the dialysis machine 11. The paddle assembly 28 can be constructed such that when the infusate caddy is placed within a receiving compartment on the dialysis machine, the paddles 21, 22, and 23 can be aligned to the respective containers for connection to the caddy connectors 24, 25, and 26. When the caddy 30 is placed into the receiving compartment 11, the paddles 21, 22, and 23 will align with each of the container connectors. By placing the paddle assembly 28 on the dialysis machine 11, the containers can be arranged within the caddy so that when the caddy is rotated, citric acid container 15 is aligned with one or more paddles 21 for connection to the dialysis machine 11. By rotating the caddy 30 so the citric acid container 15 is aligned for connection to the dialysis machine 11, the caddy 30 can be placed in a disinfection configuration, allowing citric acid to be moved from the citric acid container 15 through the container connectors 19, 20, and 35, and the caddy connectors 24, 25, and 26 on paddles 21, 22, and 23, and into the dialysis machine 11 for disinfection. The caddy 30 can include handle 30 for easy movement of the caddy 30. Citric acid container 15 can contain internal fluid pathways between any of connectors 19, 20, and 35 to allow a cleaning and/or disinfection solution to be recirculated through one or more of connectors 24, 25 and 26 by action of a single pump.

Figure 2:
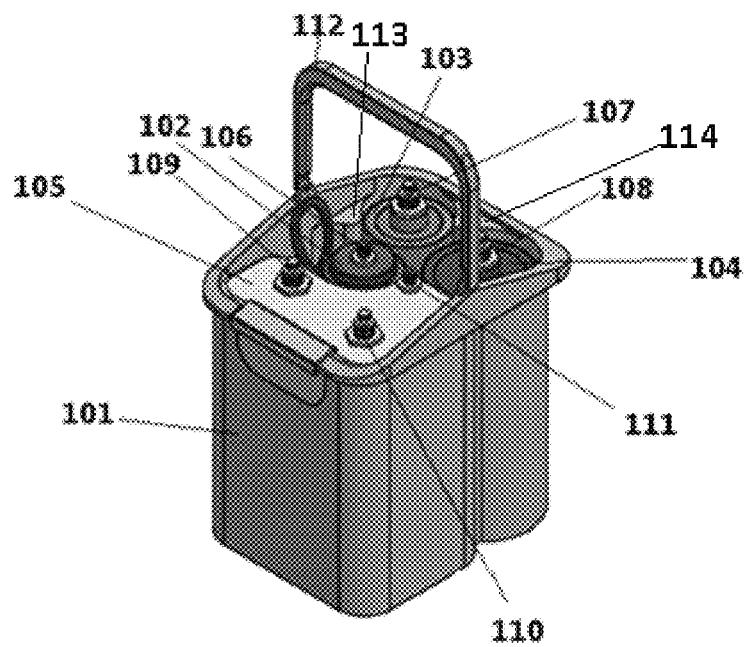
FIG. 2 shows an infusate caddy containing solute containers removed from a dialysis machine with a handle.

FIG. 2 shows infusate caddy 101 removed from a receiving compartment of a dialysis machine. As in FIG. 1, the caddy 101 of FIG. 2 includes cation infusate container 102, sodium bicarbonate container 103 and sodium chloride container 104. Protrusion 113 and protrusion 114 can provide fitting features for the respective receiving compartments for each of the cation infusate container 102, sodium bicarbonate container 103 and sodium chloride container 104. A citric acid container 105 can be optionally added for disinfection after each dialysis session. In a preferred, non-limiting embodiment, an infusate caddy only contains cation infusate container 102, sodium bicarbonate container 103 and sodium chloride container, and does not include a citric acid container. Each of the cation infusate container 102, sodium bicarbonate container 103 and sodium chloride container 104 can be connected to a dialysis system by connectors 106, 107, and 108 respectively. In FIG. 2, the paddles, described in FIG. 1, provide fluid connection between the infusate containers and the dialysis machine. The paddles can be configured so that in the lowered state the paddles align with the connectors of the containers 102, 103 and 104. The caddy 101 can be also configured in a disinfection configuration after use so that the paddles align with citric acid container 105, through connectors 109, 110 and 111. As shown in FIG. 2, the optional handle 112 can be raised for easy carrying of the caddy 101.

Figure 3:
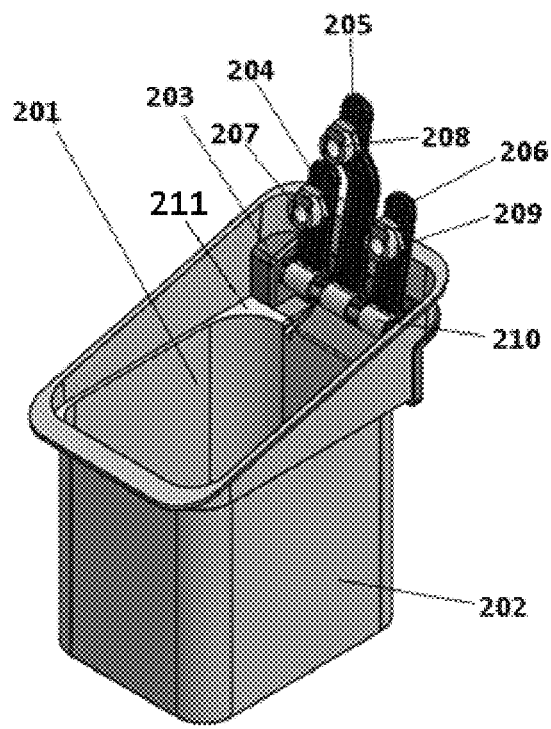
FIG. 3 shows an empty receiving compartment of a dialysis machine having an infusate caddy removed.

FIG. 3 shows an interior 201 and a paddle assembly 203 located at a top section of a receiving compartment 202 with the infusate caddy (not shown) removed. The infusate caddy can be removed from interior 201 of the receiving compartment 202 to replace the containers, refill the containers, store the caddy, clean the caddy, clean the interior 201 of the receiving compartment 202, or for any other reason. The caddy connectors 207, 208, and 209 can be disconnected from the corresponding infusate container fluid connectors as described. The paddles 204, 205, and 206 of the hinged paddle assembly 203 can be raised by pivoting on hinge 210, so that the infusate caddy can be removed from the interior 201. The receiving compartment 202 can be cleaned for reuse with the same or different infusate caddy having an appropriate fitting feature. Curved protrusion 211 can be positioned in at least one of the four corners of the interior 201 of the receiving compartment 202 as a fitting feature for receiving an infusate caddy have a substantially rectangular shaped with curved corners. As described, the fitting feature can include protrusions, indentations, grooves, ridges, size and/or shape, a depth, incline, or diameter to provide complementary surface for an infusate caddy or position of the infusate caddy inside the receiving compartment 202.

Figure 4A:
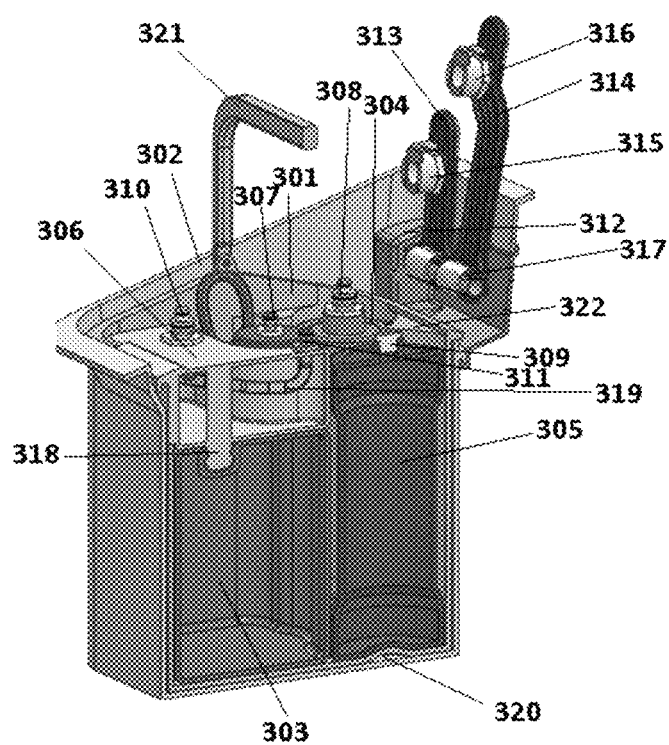
FIG. 4A shows a cut-away view of an infusate caddy containing solute containers in a dialysis configuration seated in a receiving compartment of a dialysis machine.
Figure 4B:
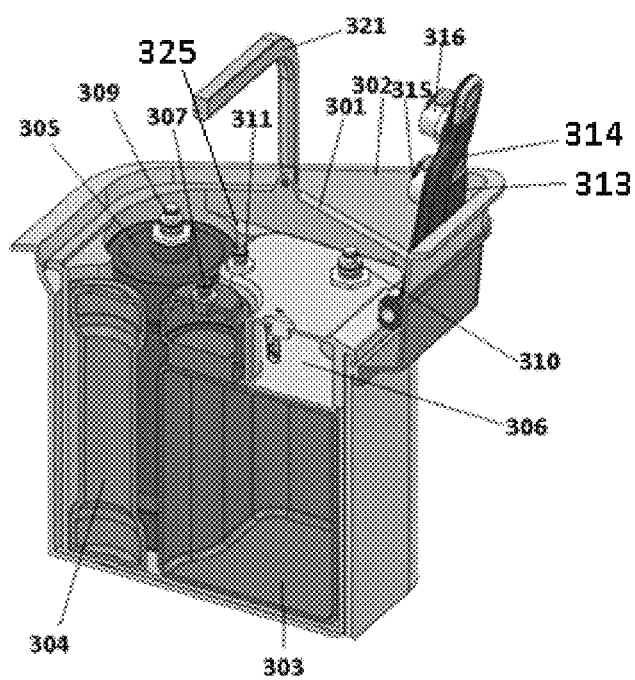
FIG. 4B shows a cut-away view of an infusate caddy containing solute containers in a dialysis machine in a disinfection configuration.
Figure 4C:
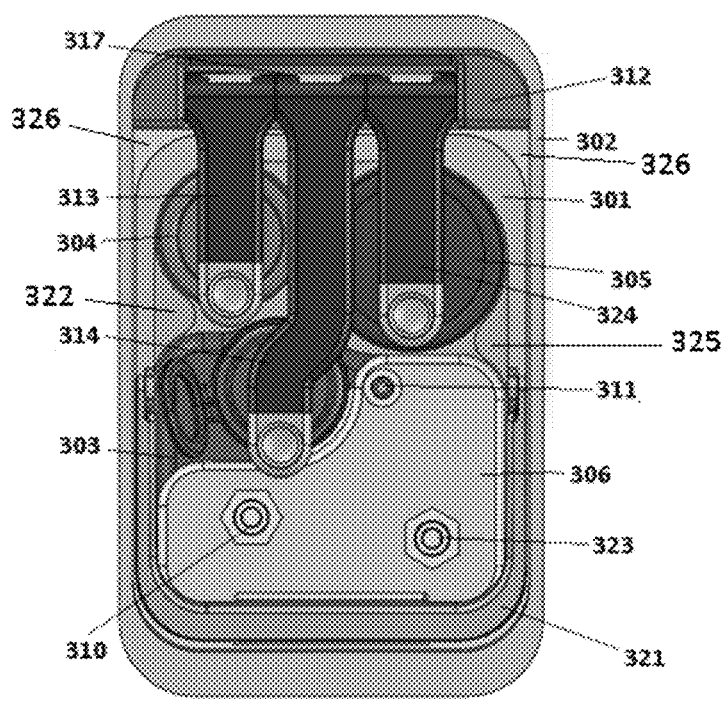
FIG. 4C shows a top view of an infusate caddy seated in a receiving compartment of a dialysis machine containing solute containers in a dialysis configuration.

FIGS. 4a and 4b show cutaway views of a caddy, while FIG. 4c shows a top view of a caddy. Components identified by the same reference numbers in FIGS. 4a, 4b and 4c correspond to the same components. FIG. 4a shows a caddy 301 in a dialysis configuration, or in a priming configuration prior to dialysis, where the caddy 301 is seated in a 302 so the cation infusate container 303, sodium bicarbonate container 304, and sodium chloride container 305 are aligned with the paddles 313 and 314. Citric acid container 306 is not connectable to any paddle in the dialysis configuration of FIG. 4a. Container connector 307 on cation infusate container 303 and container connector 308 on sodium bicarbonate container 304 can connect to fluid connectors 315 on paddle 313 and fluid connector 316 on paddle 314. Fluid connector 309 on sodium chloride container 305 can also connect to a fluid connector (not shown in FIG. 4a). The paddles can be part of paddle assembly 312. To connect the infusate containers to the paddles, the paddles can be rotated downward on hinge 317 and the fluid connectors 315 and 316 can connect to containers 303 and 304 respectively. As shown in FIGS. 4a and 4b, the caddy 301 and the infusate containers within the caddy 301 can have one or more fitting feature to ensure the containers are connected to the correct paddle. The fitting features can also have the additional benefit of ensuring a tight fit within the caddy 301 to resist inadvertent movement. The one or more fitting features can ensure each container occupies a unique position within the caddy 301. Moreover, the interior of the caddy 301 can itself be a shaped fitting feature so each container can only be placed within a specific position or receiving compartment within the caddy 301. Fitting features can be included on any connection surface of the caddy, where any container contacts the interior of the caddy 301. For example, interior of the caddy 301 can include fitting feature protrusion 320, which is a protrusion on the base of the caddy 301. For example, the base of sodium chloride container 305 can be designed with a corresponding complementary indentation, such as a similarly sized recess, while the other containers lack the complementary indentation. Container 305 will be the only container that can properly fit into the position in caddy 301 for protrusion 320. Similarly, curved wedge protrusion 322 is disposed on the side of the caddy 301 interior. The protrusion 322 separates the sidewall of the caddy 301 interior into two sections. Sodium bicarbonate container 304 can be the only container with the proper size, shape, or geometry to fit within one of the sections on the sidewall, whereas sodium chloride container 305 can be the only container with the proper size, shape, or geometry to fit within the other section. Each container can be positioned in one particular location within the caddy 301. Additionally, the containers themselves can have fitting features that ensure the proper arrangement of the containers within the caddy 301. In FIG. 4a, citric acid container 306 includes flange 318. Cation infusate container 303 has a corresponding slot. The citric acid container 306 can only be placed within the caddy 301 at the precise position above cation infusate container 303. By sizing and shaping the interior of the cavity and the containers, the containers can only be placed within the caddy 301 in a single arrangement. When the caddy 301 is seated in the receiving compartment 302, the containers and connectors align with the proper paddles for connection to a dialysis system and related flow path to ensure that the proper solutes from the containers enter the dialysate flow path at the correct locations and that the proper pumps and valves are controlling the correct solute additions. Handle 321 can be included for easy of carrying and removal of the caddy 301 from receiving compartment 302. During use, fluid lines, such as line 319 in citric acid container 306, can move fluids from the containers into the paddles.

The fitting features can include specific types of connectors on the containers and on the paddles or specific locking mechanisms on the paddles adapted for connection to a specific container. For example, connector 307 can be of a specific size, shape, geometry or type, while connector 308 can be of a different size, shape, geometry or type. Correspondingly, fluid connector 316 can be of a complementary size, shape, geometry or type to connector 307, while fluid connector 315 can be of a complementary size, shape, geometry or type to connector 308. In use, fluid connector 316 will only be able to lock onto and form a fluid connection with connector 307, while fluid connector 315 will only be able to lock onto and form a fluid connection with connector 308. That is, each paddle can include a locking mechanism adapted for a particular container, ensuring that the respective containers are connected to the correct paddles for use in dialysis.

FIG. 4b shows the caddy 301 in a disinfection configuration. The caddy 301 can be placed in a disinfection configuration by rotating the caddy 301 by 180° degrees so that paddles 313 and 314 align with connectors 309 and 310 on citric acid container 306, which can contain a disinfection solution such as citric acid, placing the paddles 313 and 314 on the opposite side of the caddy 301 as in the dialysis configuration shown in FIG. 4a. The same pumps and valves as described for movement of sodium chloride, sodium bicarbonate or cation infusates can be used to direct fluid from the citric acid container 306 into the dialysis system and related flow paths. Fluid lines within the citric acid container 306 can allow circulation between multiple connectors during cleaning or disinfection. For example, fluid can pass between connectors 311 and 310 through citric acid container 306 to allow cleaning or disinfection fluid to be circulated through connectors 315 and 316 by action of a single pump. The caddy 301 can be constructed so that one or more connectors are blocked, and therefore sealed when the caddy 301 is placed in the disinfection configuration. Only the connectors necessary to move citric acid from the citric acid container 306 to the dialysis system can be open to allow fluid movement.

As an alternative to a caddy containing a disinfection container, a second caddy can be used for disinfection. A second caddy, containing a disinfection container, can fit into the dialysis machine in the same receiving slot as the first caddy. The second caddy can include one or more fitting features to ensure that connectors on the disinfection container will align with the paddles or other fluid connectors when the second caddy is inserted into the receiving slot. However, a second caddy is not necessary, and a disinfection container can be directly connected to the fluid connectors for disinfection.

FIG. 4c shows a top view of a caddy 301 in a dialysis configuration. As is shown in FIG. 4c, sodium chloride container 305 is connected to paddle 324, cation infusate container 303 is connected to paddle 314 and sodium bicarbonate container 304 is connected to paddle 313. Citric acid container 306 is not connected to any paddles in FIG. 4c. As shown in FIG. 4c, citric acid container 306 includes three connectors 310, 311, and 323. When the caddy 301 is placed in the disinfection configuration, all of the paddles will be connected to citric acid container 306. Paddle 313 can connect to connector 323, paddle 314 can connect to connector 311, and paddle 324 can connect to connector 310. Curved wedge protrusion 328 is a fitting feature to ensure proper placement of sodium bicarbonate container 304 and cation infusate container 303. Curved wedge protrusion 329 is a fitting feature to ensure proper placement of sodium chloride container 305 and citric acid container 306. Similarly, curved corner protrusions 730 at each corner of the receiving compartment 302 can ensure the proper seating of the caddy 301.

Figure 4D:
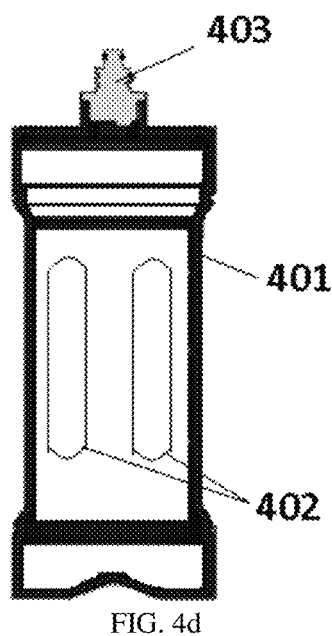
FIG. 4D shows a container with ridges on the exterior of the container to ensure complementary fitting in a caddy.

FIG. 4d shows an example of a container wherein the fitting features designed to keep the container in place are a series of ridges. Container 325 can be constructed with one or more ridges 326. The interior of the caddy corresponding to the unique location for container 325 can have a series of complementary corresponding grooves. The container 325 can only be placed in the caddy in the unique position where the complementary grooves in the interior of the caddy align with the ridges 326 on the exterior of the container 325. Other containers can have differently sized ridges, differently spaced ridges, and/or a different number of ridges. The caddy can be constructed with the proper corresponding grooves for each container in the correct location. Because the containers can only be positioned in the caddy where the corresponding ridges and grooves are complementary, these features can ensure the proper position for each container. If the caddy is connected to the dialysis machine, connector 327 on container 325 will align with the proper paddle or other connector on the system to ensure that the proper solution is added to the dialysis system in the proper amounts and at the proper location. One skilled in the art will understand that the grooves can be constructed on the containers and the ridges on the caddy.

Any mechanism for attaching the caddy to the dialysis system can be used. The infusate caddy and the dialysis machine can include a locking mechanism configured to keep the infusate caddy from moving after insertion into the receiving compartment, such that when the caddy is attached to the dialysis system the caddy becomes locked to the dialysis system, resisting inadvertent detachment when the locking mechanism is positioned in a locked state. The locking mechanism can be positionable in an open state, which will allow removal of the caddy. The dialysis machine can include a receiving compartment, such as that shown in FIG. 1, into which the caddy can be placed.

Figure 5A:
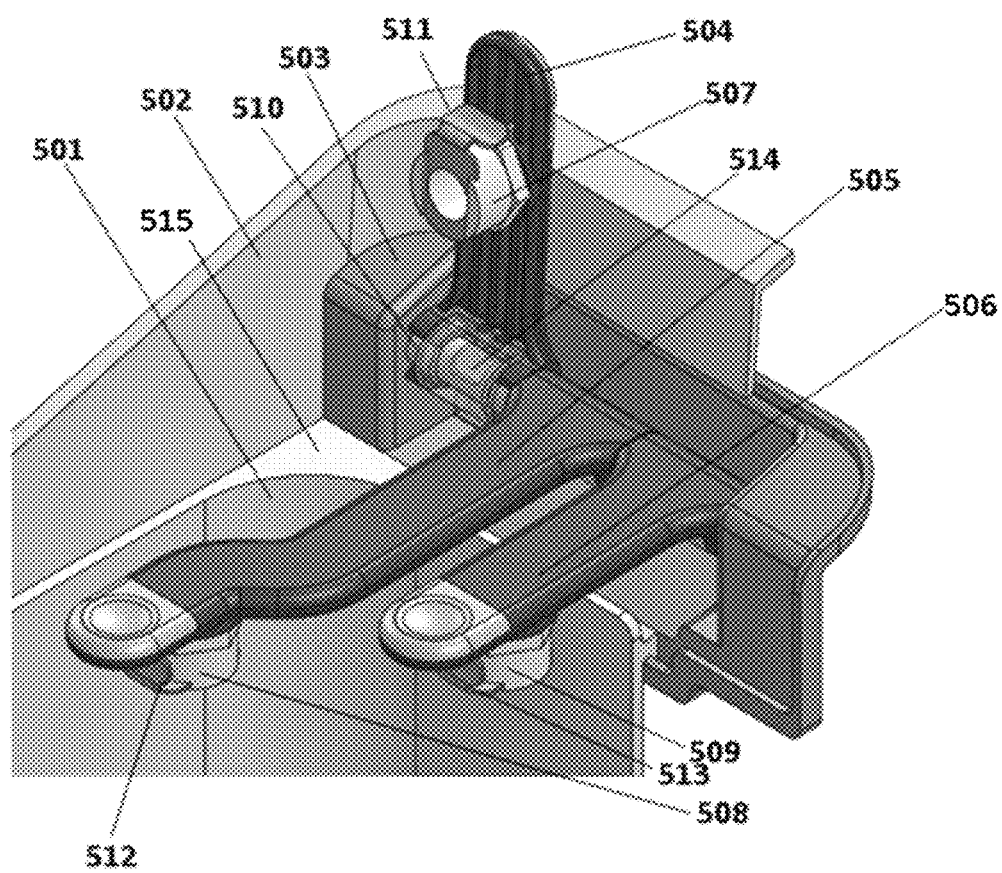
FIG. 5A shows a close-up perspective view of a paddle assembly on a portion of an infusate caddy.
Figure 5B:
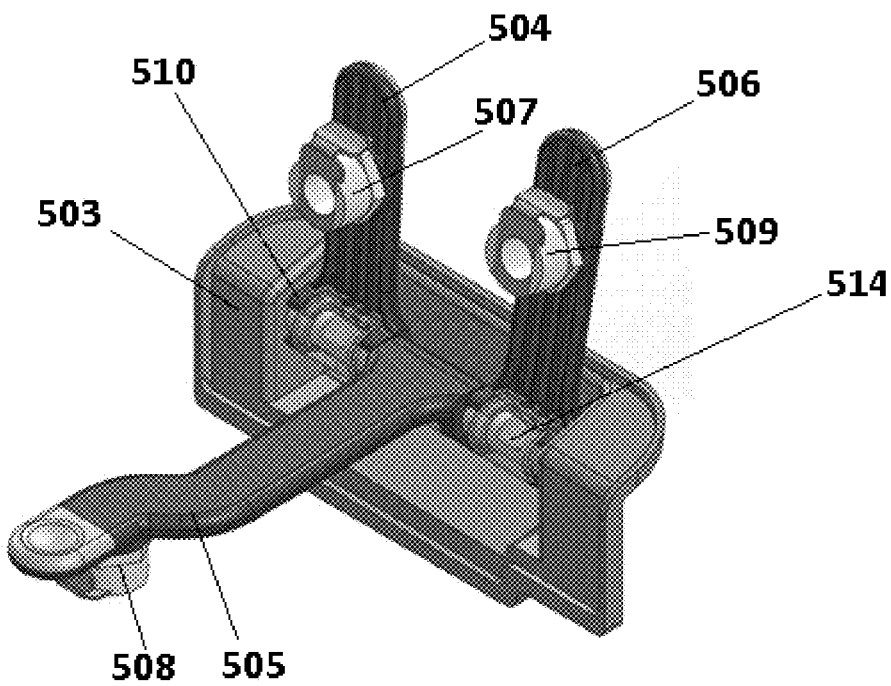
FIG. 5B shows a close-up view of a perspective paddle assembly.
Figure 5C:
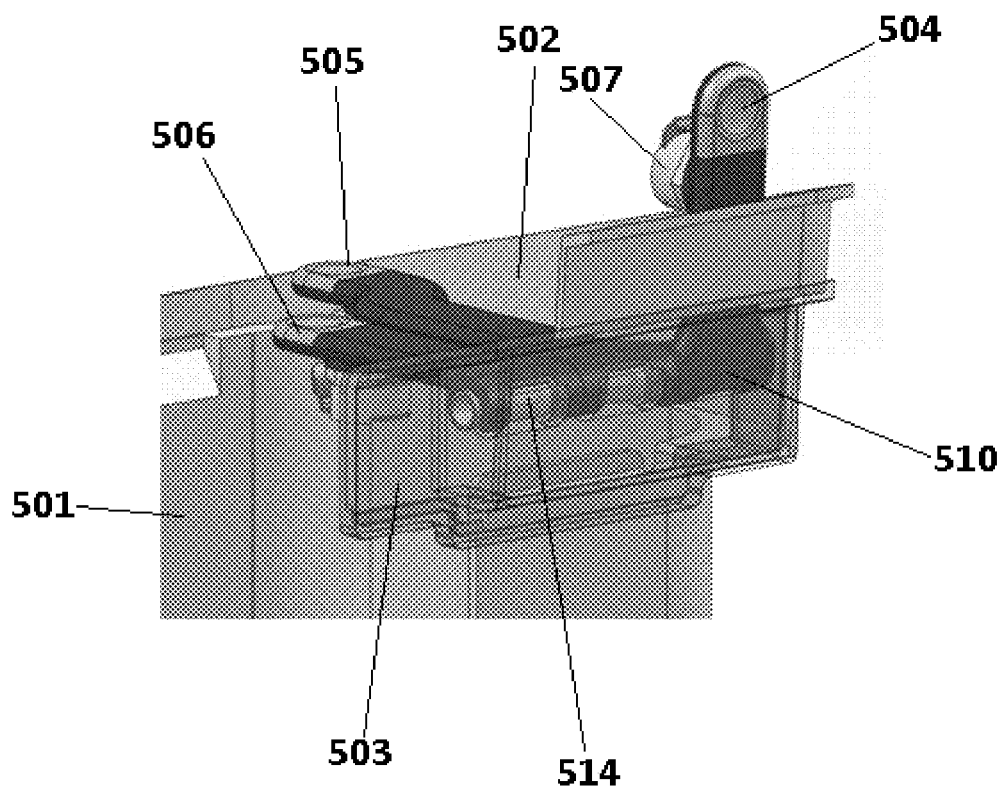
FIG. 5C shows a reverse view of a paddle assembly on an infusate caddy.

FIGS. 5a, 5b, and 5c show a close up view of the paddle assembly described. FIG. 5a shows the paddle assembly 503 with an empty caddy 501 on dialysis machine 502. One paddle 504 is shown in the up, or disconnected position. The other two paddles 505 and 506 are in the down position, or the position the paddles will be in when attached to the containers. FIG. 5b shows a floating paddle assembly 503 with paddles 504 and 506 in a disconnected position and paddle 505 in a connected position. Such configuration can be used for specific needs for a flow path only requiring connection between fluid connector 512 and a properly connected infusate container. Each paddle can be moved between positions on a hinge, such as hinge 510. FIG. 5c shows a rear view of the paddle assembly 503 showing a hinge 510 as viewed from a back side of dialysis machine and viewing the an empty receiving compartment 502. Each of the paddles can be moved independently of the other paddles, as shown in FIGS. 5a and 5b. The single hinge 510 of FIG. 5c can be used and all paddles can be moved together. As shown in FIG. 5a, each paddle 504, 505, and 506 can have a paddle connector 507, 508, and 509 for connection to a container as described. Locking mechanism components 511, 512, and 513 can lock the paddles to the container connectors as described. The locking mechanisms on each paddle can be adapted to a particular container. The paddle assembly can also include a mechanism to hold one or more paddles in the disconnected position. For example, the paddles or hinge can include a locking mechanism (not shown) that locks the paddles in either the open or closed position until a user unlocks the mechanism to allow the paddles to move. The paddles can connect tightly to the hinge. The friction caused by the connection between the paddles and the hinge can cause the paddles to remain in either the connected or unconnected position until an external force is applied to the paddles, such as by a user. Further, the curved corner protrusion 515 can ensure proper seating of an infusate caddy and hence, proper alignment of the paddle connectors 507, 508, and 509.

The described fluid lines can be placed within the paddles for easy connection of the containers to the dialysis system. Paddle 504 may connect to the cation infusate container as described. The paddle connector 507 may be in fluid communication with the corresponding connector on the cation infusate container, as shown in FIG. 4a. A fluid line may run from the paddle connector 507, through the paddle 504, and through the hollow portion 514 of hinge 510. The fluid line can further connect into the appropriate position of the dialysate flow loop. By using the paddles themselves as the fluid lines, connection of each container to the proper position in the dialysate flow loop can be assured.

Figure 6A:
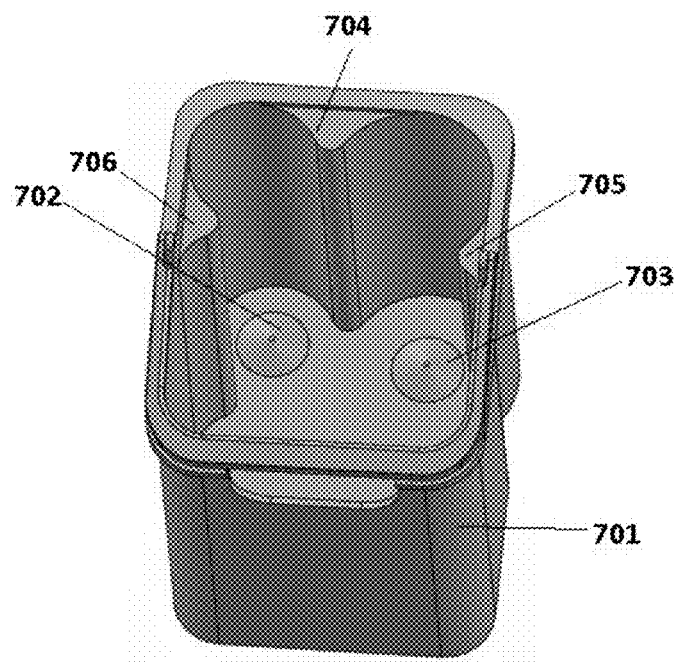
FIG. 6A shows an empty infusate caddy for container registration.

FIG. 6a shows an empty caddy 701. As described herein, the caddy can include receiving compartments, which are specific and unique positions for each of the containers adapted to receive containers. Position 703 is a receiving compartment shown for a sodium chloride container, position 702 is a receiving compartment shown for a sodium bicarbonate container, and a third receiving compartment (not shown) can be available for a cation infusate container. As described herein, the caddy can have fitting features to ensure that only the correct containers can fit within each receiving compartment. Fitting features 704, 705, and 706 can accomplish the function. Fitting features 704 and 706 define the geometry, size and shape of the container that can fit in position 702. Fitting features 704 and 705 define the geometry, size and shape of the container that can fit in position 703. As position 702 is not the same size as position 703, the sodium bicarbonate container will not fit in position 703 and the sodium chloride container will not fit in position 702.

Figure 6B:
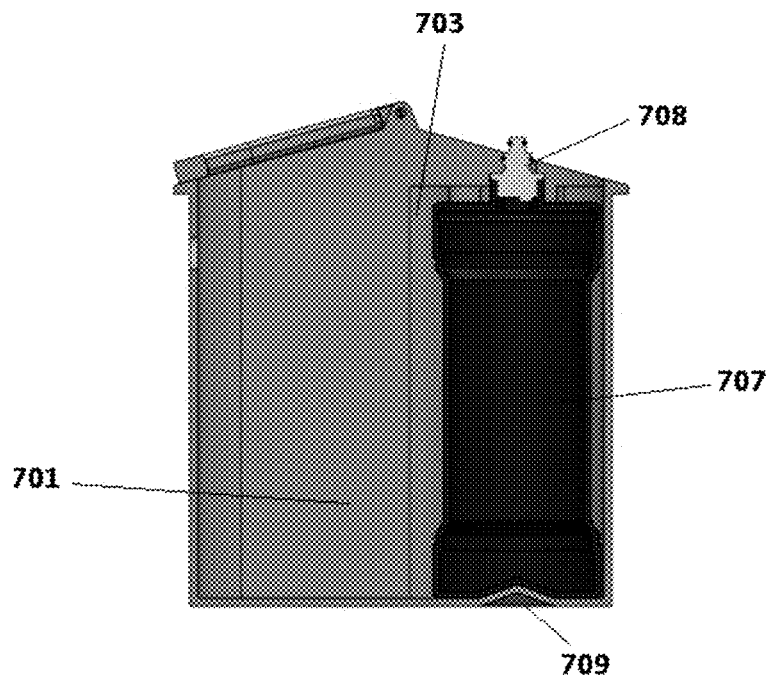
FIG. 6B shows an infusate caddy with a sodium bicarbonate container.

FIG. 6b shows a sodium bicarbonate container 707 in place in position 703. As described herein, because of the size and shape of the fitting features included in the caddy and containers, sodium bicarbonate container 707 is the only container that can fit into position 703. Once in place, a connector, such as the paddles described herein, can be connected to bicarbonate connector 708 to allow the sodium bicarbonate to be used in preparing a dialysate or used during dialysis. As described, the base of the caddy 701 can include a fitting feature 709 that corresponds to complementary fitting feature on the base of the sodium bicarbonate container 707, further ensuring that only sodium bicarbonate container 707 can fit into position 703 and to ensure that the sodium bicarbonate container 707 is properly secured within the position 703.

Figure 6C:
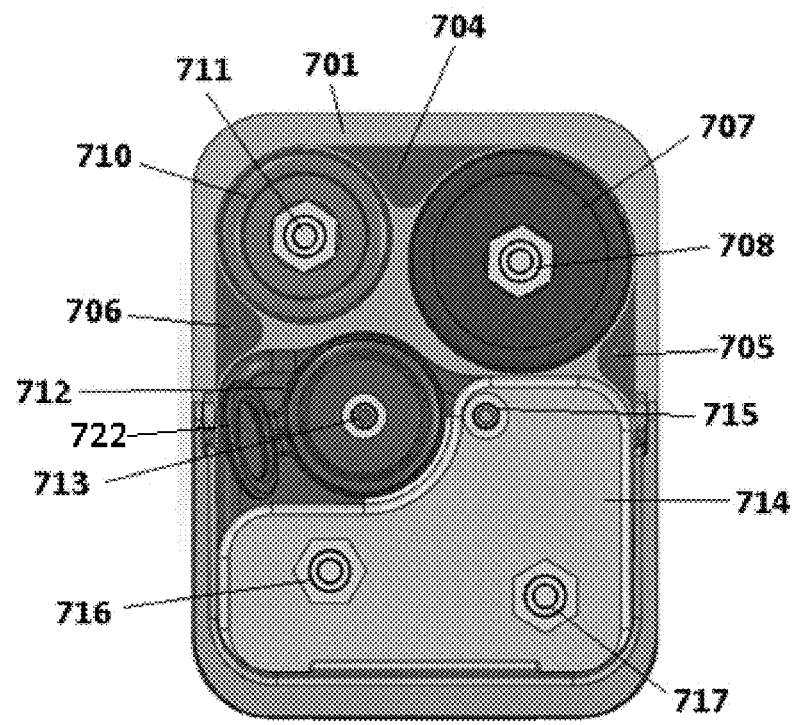
FIG. 6C shows a top view of an infusate caddy after all containers have been added to the infusate caddy.

FIG. 6c shows an infusate caddy 701 after each of the containers has been placed within the infusate caddy 701. As described sodium bicarbonate container 707 can fit into a position defined by fitting features 704 and 705. Sodium chloride container 710 can fit into a position defined by fitting features 704 and 706. Cation infusate container 712 can fit into a position defined by fitting features 705 and 706. As such, each of the containers can only fit into the proper position within the caddy, ensuring that sodium chloride connector 711, sodium bicarbonate connector 708 and cation infusate connector 313 can only connect to the proper connectors, pumps and valves of the dialysis machine. The caddy 701 can also include an optional disinfection container 714. When the caddy 701 is placed in a disinfection orientation, disinfection connectors 715, 716 and 717 can connect to the proper connectors, pumps and valves in the dialysis machine to carry out disinfection.

Figure 6D:
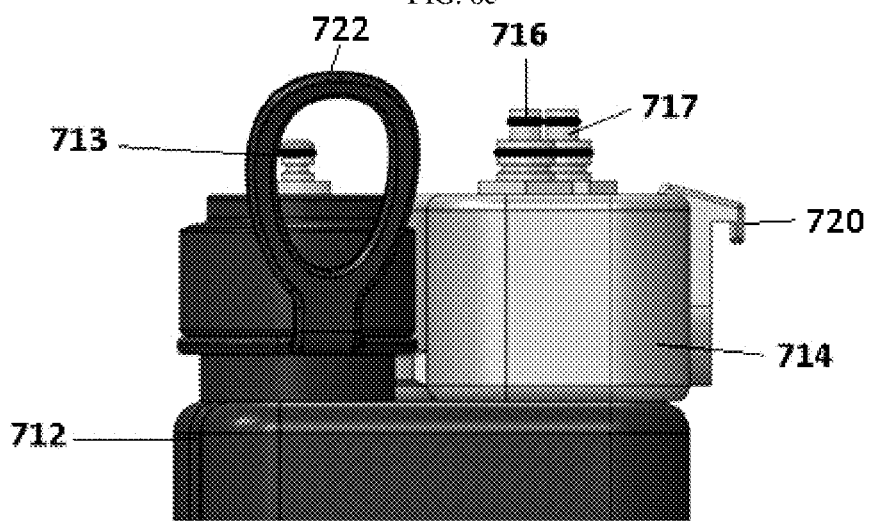
FIG. 6D shows a close up view of a disinfection container and cation infusate container fitted together.

FIG. 6d shows a close up the disinfection container 714 in an infusate caddy. To save space, the disinfection container 714 and cation infusate container 712 can include fitting features, such as by being sized and shaped so that the disinfection container 714 fits on top of cation infusate container 712. One skilled in the art will understand that any containers can be sized and shaped to fit on top of one another, and the feature is not limited to the disinfection container 714 and cation infusate container 712.

Figure 6E:
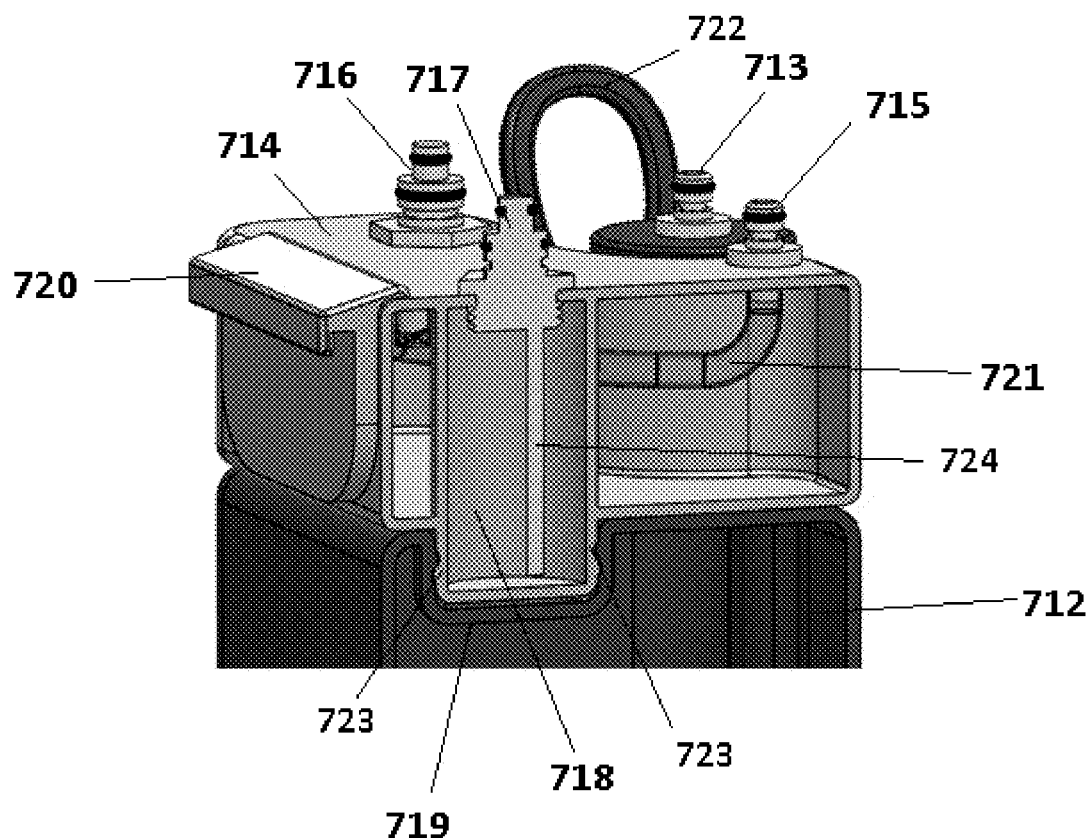
FIG. 6E shows a cut-away view of a disinfection container and cation infusate container fitted together.

To check if the disinfection container 714 is properly in seated in the infusate caddy 701 for use in disinfection, the disinfection container 714 and cation infusate container 712 can each have fitting features to ensure proper insertion and alignment of the disinfection container 714. Non-limiting examples of such fitting features are shown in FIG. 6e. As shown in FIG. 6e, disinfection container 714 can include a separate container 718, which can hold a solid disinfectant source or any other substance. Container 718, which is integral to disinfectant container 714, can fit into indentation 719 built into cation infusate container 712. Because container 718 can only fit into indentation 719 in a single configuration, in order for disinfection container 714 to fit on top of cation infusate container 712, the disinfection container 714 must be in the proper configuration for use in disinfection. Ridges and indentations 723 on container 718 and cation infusate container 712 are complementary fitting features that securely lock container 718 into place on cation infusate container 712. Fluid line 724 in container 718 provides for access to fluid in a bottom section of container 718. Disinfection container 714 can also or alternatively include fitting feature, flap 720. Flap 720 can fit over the edge of the infusate container (not shown in FIG. 6e), ensuring that the disinfection container 714 is in the proper location inside of the infusate caddy. During disinfection, disinfection fluid, such as citric acid, can flow through line 721 and into the dialysis system. Any one or more of the infusate containers can include a handle, such as handle 722 on cation infusate container 712.

Each of the connectors can have a size and shape keyed to a particular fluid connector on the dialysis machine. In FIGS. 6a-e, connectors 713 and 715 are rounded, while connectors 708, 711, 716, and 717 are hexagonal. Each of the corresponding fluid connectors disposed on the dialysis machine can have a size and shape to only engage with the connectors on the proper infusate containers. As illustrated in FIGS. 6a-e, each of fluid connectors on the infusate containers can include an o-ring or other sealing mechanism to prevent leakage when connected.

Figure 7:
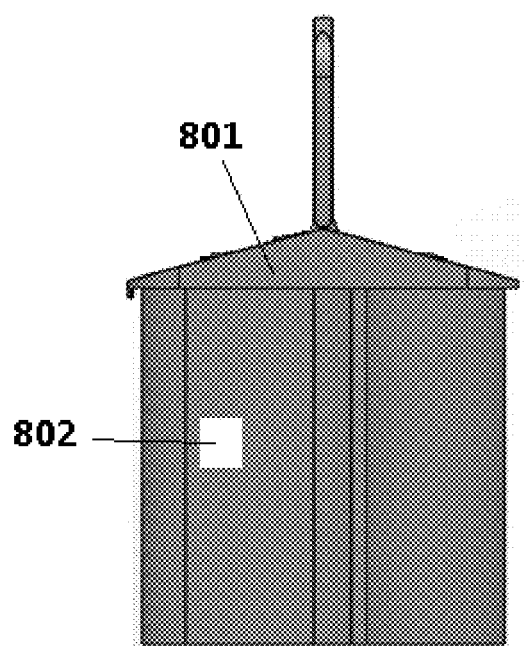
FIG. 7 shows a caddy with a sensor for sensing an orientation of the caddy.

The infusate caddy can include a sensor, as shown in FIG. 7 to detect whether the caddy is in a dialysis orientation or a disinfection orientation. Caddy 801 can include sensor 802 affixed to the caddy. Although in FIG. 7, the sensor is shown on the side of the caddy, one skilled in the art will understand that the sensor can be placed anywhere on the caddy, including the base of the caddy or the inside portion of the caddy. Sensor 802 can interact with a corresponding sensor, detector, or other component on the dialysis machine (not shown). When the caddy is placed into the dialysis machine, the position of the sensor 802 can be detected, thus determining the orientation of the caddy. The dialysis machine can be configured to become disabled if the caddy is in an incorrect orientation. For example, the dialysis machine can shut down if a user attempts to begin a dialysis session while the caddy is in the disinfection orientation. Similarly, the dialysis machine can shut down if the user attempts to disinfect the system while the caddy is in the dialysis orientation.

The sensor 802 can be any type of sensor known in the art for determining the orientation of the caddy, including a Hall sensor. A Hall sensor is a component that varies a voltage output based on distance from a magnetic field. As such, either the dialysis machine or the sensor component 802 can emit a magnetic field. The Hall sensor, located on the other component from the magnetic field emitter can thus determine the distance from the magnetic field emitter. The distance from the magnetic field emitter can inform the system and user of the caddy orientation. Alternatively, the sensor 802 can be a magnetic sensor. A corresponding magnet can be placed on the dialysis machine. When the caddy is placed in the dialysis machine, the magnetic sensor can determine whether the magnet is aligned with the sensor, and thus the orientation of the caddy.

The caddy can additionally or alternatively include a tracking component, such as a barcode or radio frequency identification component (RFID). The tracking component allows for the system to match the infusates or other components in the caddy with a particular patient and machine. Before use, the user can be prompted to scan the barcode or RFID. The system can ensure that the proper caddy is matched to the particular patient, thus ensuring that the patient receives the correct infusates based on the patient's dialysis prescription. The dialysis machine can also include a tracking component. Before use, the system can ensure that the infusate caddy is matched to the particular dialysis machine, ensuring that the proper patient is using the proper dialysis machine with the proper caddy containing the proper sets of containers. The tracking component can be a writable RFID. The system can write a patient specific identifier onto the tracking component. When the infusate caddy is filled with containers, the RFID on the caddy can be checked against the patient prescription to ensure that the proper containers are filled and placed within the caddy for a specific patient. When the caddy is filled with the solute containers, the prescription can be electronically programmed or written onto the RFID. When the caddy is inserted into the dialysis machine, the system can read the prescription and ensure that the prescription matches with the correct patient.

Figure 8:
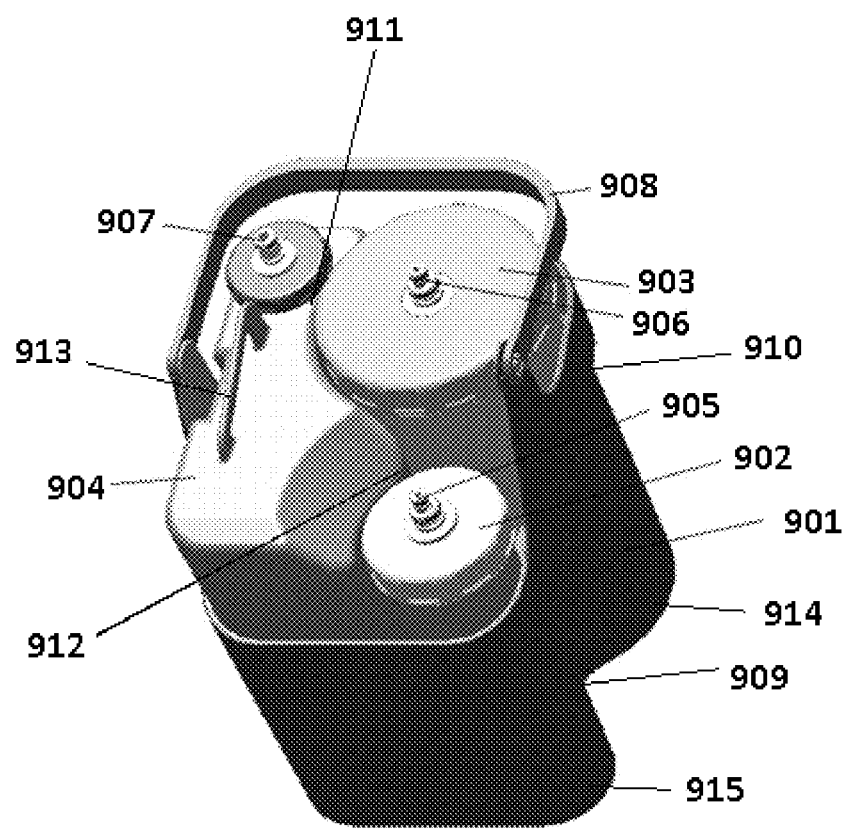
FIG. 8 shows an infusate caddy with a bicarbonate container, a sodium chloride container, and a cation infusate container.

FIG. 8 illustrates an infusate caddy 901 with a sodium chloride container 902, a sodium bicarbonate container 903, and a cation infusate container 904. A citric acid container is not included in the embodiment shown in FIG. 8. Each of the sodium chloride container 902, sodium bicarbonate container 903, and cation infusate container 904, can be connected to a dialysis system by connectors 905, 906, and 907 respectively. As described, the infusate caddy 901 can include a collapsible handle 908 integral to the infusate caddy 901 for easy removal from a dialysis machine. The infusate caddy 901 can be a size and shape complementary to a receiving compartment in a dialysis machine (not shown in FIG. 8). The infusate caddy 901 can include one or more fitting features forming receiving complementary to each of the infusate containers. The infusate caddy 901 can include a protrusion 910 in a side of the infusate caddy 901 complementary to an indentation in a receiving slot of a dialysis machine. The protrusion 910 can also correspond to a complementary protrusion on the side of sodium bicarbonate container 903. The infusate caddy can also have an indentation 909 separating the infusate caddy 901 into a first section 914 and second section 915. The indentation 909 can serve as a fitting feature complementary to a shape of a dialysis machine receiving compartment, as well as complementary to a size and shape of each infusate container. As illustrated, the first section 914 can have a base at a higher elevation than second section 915. The receiving compartment of the dialysis machine can be shaped complementary to the two sections of the infusate caddy 901, with a first section having a base at a higher elevation than a second section. The difference in elevations of the first section 914 and second section 915 place the top of sodium bicarbonate container 903 at a higher elevation than the top of sodium chloride container 902. As described, each of the dialysis machine connectors can be sized to only reach a specified length, and the dialysis machine connector for the sodium bicarbonate container 903 can be shorter than the dialysis machine connector for sodium chloride container 902, ensuring that the sodium chloride container 902 cannot be connected to the dialysis machine connector for sodium bicarbonate container 903.

The infusate containers can have one or more fitting features complementary to another infusate container. Fitting feature 911 is a circular indentation in cation infusate container 904. The circular indentation 911 is complementary to a size and shape of sodium bicarbonate container 903. Cation infusate container 904 also includes circular indentation 912 complementary to a size and shape of sodium chloride container 902. The radii of circular indentations 911 and 912 is such that sodium bicarbonate container 903 cannot fit in the infusate caddy 901 at any position other than at circular indentation 911, and that sodium chloride container 902 cannot fit in the infusate caddy 901 at any location other than at circular indentation 912. The fitting features on the infusate container can be selected from any one of a specified geometry, size, or shape of any one of the infusate container with respect to a complementary geometry, size, or shape of another infusate container. Hence, infusate containers can each individually have a fitting feature such that the containers for a system of fitting features. Moreover, the system of fitting features can be specific to a particular treatment, disinfecting, or storing configuration. For example, cation infusate container can have one or more circular indentation complementary to a radius of a cylindrically shaped sodium bicarbonate container wherein the cylinder shape of the sodium bicarbonate container is a fitting feature for use in dialysis. A second circular indentation on the cation infusate container can be a second fitting feature complementary to a cylindrically shaped sodium chloride container wherein the cylinder shape of the sodium chloride chamber is a fitting feature. Such arrangement can be specific for use only during dialysis.

The infusate containers can have one or more combination of circular indentations fitting a complementary shape of another container to be used only during disinfection. The circular indentations can trace an arc of any length or radius. For example, the sodium chloride container 902 of FIG. 8 has a first radius that is smaller than a radius of the sodium bicarbonate container 903. The respective arcs of the circular indentation on the cation infusate container 904 can be 70-85° for circular indentation 911 and a 30-60° for circular indentation 912. One of ordinary skill will understand that any arc degree can be used for the invention to be complementary to a cylindrically shaped container of any radius. The type of sized or shaped indentations or the number of such sized or shaped indentations is non-limiting. In other words, each type and number of fittings features can be incorporated into any one of the containers contemplated by the invention. Similarly, the infusate caddy can have any type of sized or shaped indentations or number of such sized or shaped indentations complementary to a receiving compartment on a dialysis machine. As such, the receiving compartment on the dialysis machine can, in turn, have any type, shape, or number of fitting features. For example, the shape of the fitting feature of the caddy or receiving compartment on the dialysis machine can include a cube, disc, ovoid, or triangular prism shape. The bottom and upwardly extending wall of the infusate caddy can also have any number of fitting features that is complementary to the receiving compartment of the dialysis machine.

Any of the infusate containers can include a handle for easy removal and movement of the infusate containers, shown as handle 913 on cation infusate container 904. As illustrated in FIG. 8, each container can include a removable top, including the screw tops shown in FIG. 8, for addition of chemicals or cleaning of the infusate containers.

Each of the infusate containers can be any volume, depending on the needs of the system or patient. The sodium bicarbonate container can be any volume, including between 10 mL and 4,000 mL. A system with a small dialysate flow path may only require about 10 mL of sodium bicarbonate concentrate for priming. However, for larger systems, systems that require conditioning of a sorbent cartridge, and if the patient requires additional bicarbonate to correct acidosis, a large amount of sodium bicarbonate concentrate may be necessary. Sodium chloride container can have a volume of between 10 mL and 500 mL, depending on the size of the flow path. For larger systems, and for priming of sorbent cartridges, flush reprocessed dialyzers, and for providing a fluid bolus to a patient, large amounts of sodium chloride may be necessary, requiring up to 500 mL of the sodium chloride concentrate. The cation infusate container can be any volume between 10 mL and 4,000 mL, depending on the concentration of cations in the cation infusate container and the needs of the patients.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. An infusate caddy, comprising:
    a bottom and at least one wall extending upwardly from the bottom to form a shape complementary to a receiving compartment on a dialysis machine, wherein the at least one wall is configured to form an interior surface inside the infusate caddy; and
    at least one fitting feature disposed on the interior surface of the infusate caddy; the at least one fitting feature defining at least two receiving compartments in the infusate caddy; wherein every receiving compartment included in the infusate caddy has a size and/or shape different from every other receiving compartment included in the infusate caddy; each of the at least two receiving compartments in the infusate caddy complementary to one of at least two infusate containers; wherein each of the at least two infusate containers contact the interior surface of the infusate caddy;
    wherein each of the at least two infusate containers occupy a unique position and fit inside the infusate caddy and resist inadvertent movement of the at least two infusate containers; wherein the at least one fitting feature disposed on the interior surface of the infusate caddy is configured to define only one arrangement of the at least two infusate containers within the infusate caddy.

2. The infusate caddy of claim 1, wherein the shape complementary to the receiving compartment on the dialysis machine is any one of a cube, disc, ovoid, or triangular prism.

3. The infusate caddy of claim 1, wherein each of the at least two receiving compartments in the infusate caddy is aligned to a fluid connector disposed on the dialysis machine; and wherein the fluid connector forms a fluid connection between each of the at least two infusate containers and a flow path inside the dialysis machine.

4. The infusate caddy of claim 1, wherein the at least one fitting feature is any one or more selected from the group consisting of:
    (i) a protrusion, an indentation, a groove, and a ridge complementary to a corresponding indentation, a corresponding protrusion, a corresponding ridge, or a corresponding groove on one of the at least two infusate containers;
    (ii) a specified geometry, size, or shape complementary to a corresponding geometry, a corresponding size, or a corresponding shape of one of the at least two infusate containers;
    (iii) a visual indicator indicative of proper seating of one of the at least two infusate containers in the infusate caddy;
    (iv) a locking mechanism keyed to the at least two infusate containers; and
    (v) a specified geometry, size, or shape of a first infusate container of the at least two infusate containers and a complementary geometry, size, or shape of a second of the at least two infusate containers.

5. The infusate caddy of claim 1, further comprising an infusate caddy locking mechanism.

6. The infusate caddy of claim 1 wherein the at least two infusate containers are selected from the group consisting of a sodium bicarbonate container, a sodium chloride container, and a cation infusate container.

7. The infusate caddy of claim 6, wherein the at least two receiving compartments comprise a receiving compartment for a citric acid container.

8. The infusate caddy of claim 7, wherein the citric acid container has at least one fluid connection to allow recirculation between two or more fluid connectors.

9. A dialysis system comprising:
the infusate caddy of claim 1 having the at least two infusate containers each containing one or more solutes;
the dialysis machine, comprising:
(i) a dialysate flow path;
(ii) the receiving compartment on the dialysis machine positioned on a top console portion of the dialysis machine adapted to receive the infusate caddy;
(iii) at least two fluid connectors fluidly connectable to the at least two infusate containers, the at least two fluid connectors fluidly connecting the at least two infusate containers to the dialysate flow path; wherein the at least two fluid connectors are positioned on at least one paddle assembly, the at least one paddle assembly configured to pivot on a hinge and resist inadvertent disconnection by a locking mechanism; and
(iv) one or more pumps and one or more valves positioned on the one or more fluid connectors; the one or more pumps and one or more valves controlling fluid flow from the at least two infusate containers into the at least two fluid connectors.

10. The system of claim 9, further comprising a control system, wherein the control system controls the one or more pumps and the one or more valves to selectively flow fluid from the at least two infusate containers into the dialysate flow path.

11. The system of claim 9, wherein the at least two fluid connectors comprise a length of hose, wherein each length of hose is alternatively connectable to each of the at least two infusate containers.

12. The system of claim 9, further comprising the locking mechanism configured to keep the infusate caddy from moving after insertion into the receiving compartment when the locking mechanism is in a locked state; wherein the locking mechanism is positionable in an open state wherein the open state allows removal of the infusate caddy.

13. The system of claim 9, wherein at least one pump of the one or more pumps is capable of moving fluid bi-directionally through the one or more fluid connectors.

14. The system of claim 9, wherein the infusate caddy is insertable into the receiving compartment on the dialysis machine in at least a first orientation and a second orientation; wherein in the second orientation, the infusate caddy is rotated between from about 1° to about 359° from the first orientation; wherein at least one of the at least two infusate containers are connectable to the dialysis machine in the first orientation, but not in the second orientation; and wherein at least one of the at least two infusate containers are connectable to the dialysis machine in the second orientation but not in the first orientation.

15. The system of claim 14, wherein at least one of the at least two fluid connectors are sealed when the infusate caddy is inserted into the receiving compartment on the dialysis machine in the second orientation.

16. The system of claim 14, wherein the at least two fluid connectors are connected to allow recirculation flow between the at least two fluid connectors when the infusate caddy is inserted into the receiving compartment on the dialysis machine in the second orientation.

17. The system of claim 14, wherein the infusate caddy contains a disinfection container connectable to the one or more fluid connectors when the infusate caddy is in the second orientation.

18. The system of claim 9, further comprising a second infusate caddy, wherein the second infusate caddy comprises one or more containers fluidly connectable to the at least two fluid connectors; and wherein the receiving compartment on the dialysis machine is adapted to receive the second infusate caddy.

19. The system of claim 18, wherein the second infusate caddy contains a disinfection container.

20. The system of claim 14, wherein the infusate caddy comprises a sensor; wherein the sensor determines whether the infusate caddy is in the first orientation or the second orientation.

21. The infusate caddy of claim 1, wherein a second infusate container of the at least two infusate containers fits in a second unique position inside the infusate caddy, wherein a first infusate container of the at least two infusate containers fits in a first unique position inside the infusate caddy; and wherein the first infusate container does not fit in the second unique position and the second infusate container does not fit in the first unique position.

22. The infusate caddy of claim 1, wherein a corresponding fitting feature disposed on a first of the at least two infusate containers is designed to mate or connect to the at least one fitting feature in the infusate caddy when the first infusate container is placed inside one of the at least two receiving compartments of the infusate caddy, the unique position defined by the at least one fitting feature.

23. The infusate caddy of claim 1, wherein the bottom and the at least one wall extending upwardly form a rectangular base having four sides of a cubic volume.

\* \* \* \* \*